United States Patent [19]

Oh

[11] Patent Number: 4,473,068
[45] Date of Patent: Sep. 25, 1984

[54] TROCHANTERIC BASKET

[76] Inventor: Indong Oh, 851 Lyndon St., South Pasadena, Calif. 91030

[21] Appl. No.: 340,025

[22] Filed: Jan. 18, 1982

[51] Int. Cl.³ .............................................. A61F 5/04
[52] U.S. Cl. ................................ 128/92 D; 128/92 R
[58] Field of Search ............... 128/92 D, 92 R, 92 C, 128/92 B

[56] References Cited

U.S. PATENT DOCUMENTS

| 583,455 | 6/1897 | Bush | 128/92 D |
| 2,561,550 | 7/1951 | Wright | 128/92 D |
| 3,741,205 | 6/1973 | Markoff et al. | 128/92 D |
| 3,955,567 | 5/1976 | Richmond et al. | 128/92 D |
| 3,987,499 | 10/1976 | Scharbach et al. | 128/92 D |
| 4,047,524 | 9/1977 | Hall | 128/92 D |
| 4,135,506 | 1/1979 | Ulrich | 128/92 D |
| 4,269,180 | 5/1981 | Dall et al. | 128/92 D |

FOREIGN PATENT DOCUMENTS

| 2247176 | 3/1974 | Fed. Rep. of Germany | 128/92 D |
| 2386301 | 11/1978 | France | 128/92 D |
| 197709 | 10/1977 | U.S.S.R. | 128/92 D |

Primary Examiner—C. Fred Rosenbaum
Assistant Examiner—C. W. Shedd
Attorney, Agent, or Firm—Gordon L. Peterson

[57] ABSTRACT

An implant for use in retention of the greater trochanter comprising a circumferentially extending band and first and second bands extending between opposite regions of the circumferentially extending band. One or more prongs are coupled to the bands. The implant cooperates with a wire for tying the implant in position over the greater trochanter. The bands of the implant are deformable so that they can be conformed to approximate the contour of the greater trochanter. The prongs are adapted to penetrate the abductor muscle-tendon attached to the greater trochanter to help retain the greater trochanter in position.

17 Claims, 6 Drawing Figures

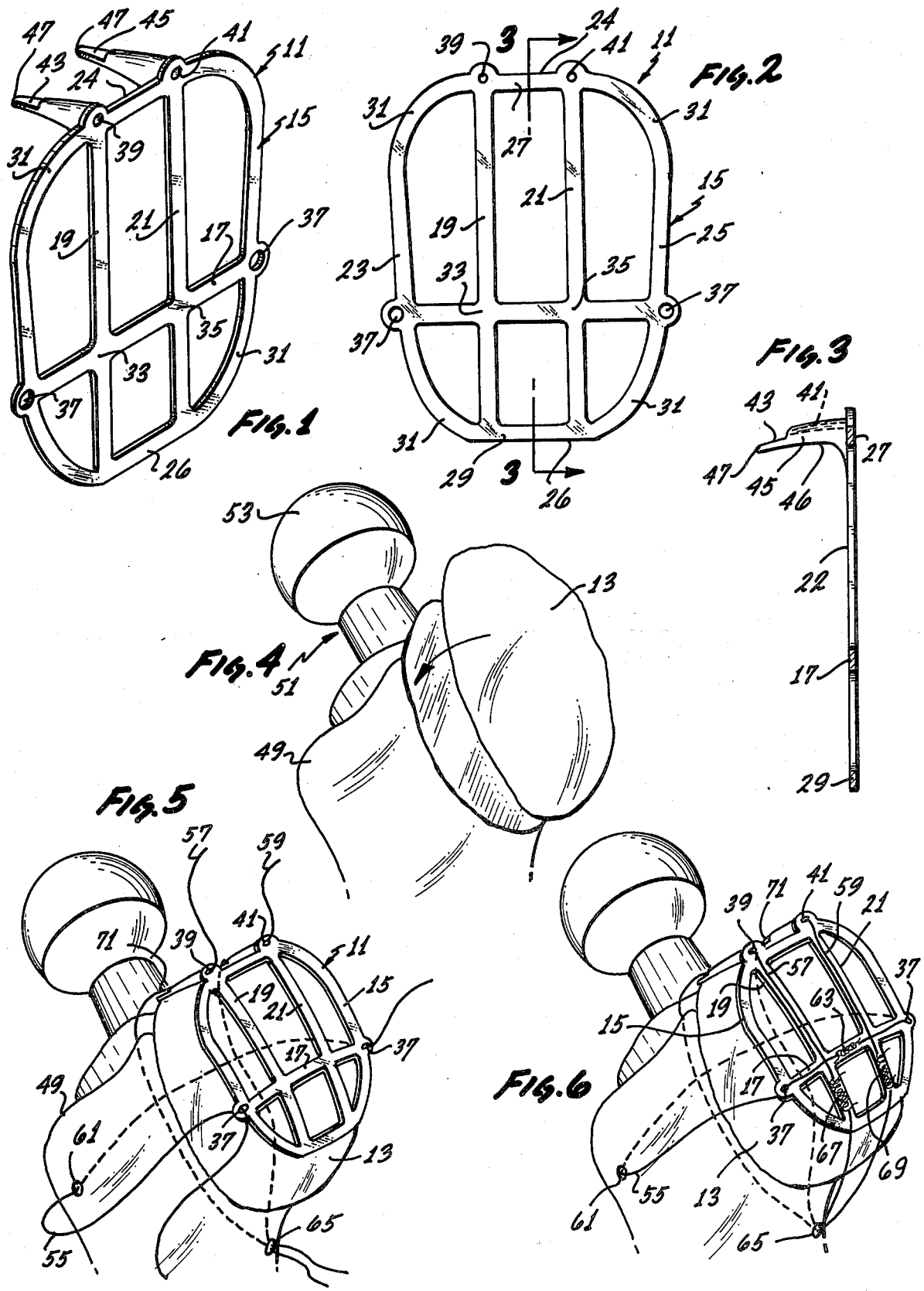

TROCHANTERIC BASKET

BACKGROUND OF THE INVENTION

In total hip arthroplasty, the greater trochanter with its attached abductor musculature is often osteotomized from the proximal femur and retracted out of the way for access to the hip joint. After the femoral head is replaced with a prosthetic femoral component, the greater trochanter is relocated and fastened in place.

The surgical problem encountered is fixation of the greater trochanter to the proximal femur until the bone has had time to fully heal. Perhaps the most common prior art method is to wire the greater trochanter in position using various techniques. In use, the abductor muscle may apply substantial force to the wires, and this can cause the wires to be pulled through the bone against which it bears. Also, if the greater trochanter is not wired tightly in position, the force of the abductor muscles against the wire can cause migration of the greater trochanter. In either event, proper fixation of the greater trochanter to the proximal femur is not obtained.

Other approaches for holding the greater trochanter include the use of trochanteric mesh and various bolting techniques, such as those shown in Lee, et al., U.S. Pat. No. 3,939,498 and Grobbelaar U.S. Pat. No. 4,153,953. The bolting techniques do not employ wire, and the trochanteric mesh does not prevent wire from pulling through the greater trochanter.

Dall, et al., U.S. Pat. No. 4,269,180 shows a rigid H-shaped implant which has projecting teeth at its opposite ends. Wire can be passed through two holes in a web of the implant and through a hole in the femur. This device requires the placement of two of the teeth into the bone, and it has a rigid appearance that would apparently substantially inhibit its conformity to the configuration of the greater trochanter. There is also no provision for holding the implant in multiple directions using wire.

SUMMARY OF THE INVENTION

This invention provides a novel implant for cooperation with wires or other elongated elements for use in retention of the greater trochanter. The implant is adapted to overlie the greater trochanter and a portion thereof is adapted to be deformed into approximate conformity with the contour of the greater trochanter. With this invention, the bone-penetrating teeth of the prior art are eliminated.

The implant can advantageously include at least first and second deformable bands having opposite ends and extending in different directions. The bands are joined together at a first location which is preferably intermediate the ends of at least one of the bands and are adapted to overlie the greater trochanter. Because the bands are deformable, they can be deformed to approximate the contour of the greater trochanter. This maximizes the area of contact between the bands and the trochanter, makes the implant adaptable to greater trochanters of different configurations, and causes the implant to grip the trochanter.

Means is coupled to each of the bands for cooperating with at least one elongated element to facilitate tying of the implant in position over the greater trochanter. Although the elongated element, such as a wire, exerts force on the bands, the bands spread this force over a large enough area of the greater trochanter with an objective of substantially reducing the likelihood of damage to the greater trochanter.

To strengthen the implant and to enable the implant to better cooperate with the greater trochanter, the implant preferably includes a deformable circumferentially extending band coupled to the first and second bands radially outwardly of the location at which the first and second bands are joined together. In one preferred construction, the circumferentially extending band completely circumscribes a region of at least the first band. The use of bands as compared with a solid sheet is greatly preferred because the geometry of the greater trochanter would require that the sheet be folded in order to conform to the trochanter.

To better enable the bands to conform to the general contour of the greater trochanter, the implant is preferably slightly elongated and the circumferentially extending band has longitudinal band sections which are inclined toward each other. Preferably the corners of the circumferentially extending band are rounded. To further improve the strength of the implant, a third band is provided which preferably extends parallel to the second band and is joined to the first band at a second location. Additional bands can be provided, if desired. The parallel second and third bands are longer than the first band and the first and second locations are spaced from the mid-point of the second and third bands.

To help retain the greater trochanter in position, the implant preferably includes means, such as one or more prongs of sufficient rigidity to penetrate the abductor muscle-tendon. Preferably, there are two prongs attached adjacent one end of the second and third bands, respectively. The prongs extend transversely to all of the bands. Although the prongs penetrate the abductor muscle-tendon, they do not penetrate the bone and they have sufficiently broad surfaces to avoid cutting through the greater trochanter.

The wire can be coupled to the implant in various different ways. However, preferably the wire attachment means is located adjacent one or more ends of the bands. This enables the bands to resist the tensile force applied by the wires, and the relatively broad bands can protect the greater trochanter from the wire. For example, openings can be formed adjacent the ends of the first band and adjacent the ends of the second and third bands where the prongs are located. The openings adjacent the prongs can take the form of tunnels which extend along lengths of the prongs so that the prongs can shield the bone from the cutting effect of the wire The invention, together with additional features and advantages thereof, may best be understood by reference to the following description taken in connection with the accompanying illustrative drawing.

BRIEF DESCRIPTION OF THE DRAWING

FIG. 1 is a perspective view of an implant constructed in accordance with the teachings of this invention.

FIG. 2 is a front elevational view of the implant.

FIG. 3 is a sectional view taken generally along line 3—3 of FIG. 2.

FIG. 4 is a fragmentary perspective view of the proximal femur following placement of a femoral component into the femur and showing replacement of the greater trochanter.

FIG. 5 is a perspective view similar to FIG. 4 with the greater trochanter in position and showing the implant being tied in position.

FIG. 6 is a perspective view similar to FIG. 5 with the implant and the greater trochanter tied in position.

DESCRIPTION OF THE PREFERRED EMBODIMENT

FIGS. 1–3 show an implant 11 for use in retention of the greater trochanter 13 (FIG. 4). The implant 11 is preferably integrally constructed from a single thin piece of biocompatible metal, such as stainless steel or chrome cobalt steel, the bands of which are sufficiently deformable or malleable so that it can be manually bent into substantial conformity with the greater trochanter 13.

The implant 11, in the preferred construction, comprises a circumferentially extending band 15 which completely circumscribes a region, a transverse band 17, and two longitudinal bands 19 and 21. Although various constructions are possible, the bands 15, 17, 19, and 21 preferably lie in the same plane. Each of the bands 15, 17, 19, and 21 has a flat surface 22 for engaging the trochanter 13 and is preferably generally rectangular cross-sectional configuration.

The circumferentially extending band 15 is slightly elongated to define opposite ends 24 and 26 and has side sections 23 and 25 joined to linear end sections 27 and 29 by rounded corner sections 31. The side sections 23 and 25 taper toward each other as they extend downwardly as viewed in FIG. 2.

The band 17 extends transverse to the longitudinal axis of the implant 11. In the embodiment illustrated, the band 17 is linear and lies approximately two-thirds of the way from the end section 27 to the end section 29. Of course, additional transverse bands may be provided, if desired.

The bands 19 and 21 extend transversely to the band 17, and in the embodiment illustrated, are linear and perpendicular to the band 17. Thus, the bands 19 and 21 are parallel, although this relationship is not critical. The bands 19 and 21 are integrally joined to the band 17 at locations 33 and 35, respectively. Although different constructions are possible, in the embodiment illustrated, the bands 19 and 21 terminate at the opposite ends of the end sections 27 and 29 contiguous the end portions of the rounded corner sections 31.

To facilitate wiring of the implant 11 in position, eyelets 37 are formed integrally with the circumferentially extending band 15 which integrally couples the eyelets to the opposite ends of the band 17. Similarly, elongated tunnels 39 and 41 are formed integrally with the circumferentially extending band 15 which couples these tunnels to the upper or proximal ends of the bands 19 and 21, respectively. No opening for wire is required at the distal ends of the bands 19 and 21. Although the eyelets 37 and the tunnels 39 and 41 could be located at other positions, they are preferably located in alignment with, and adjacent the ends of, the bands 17, 19 and 21 as shown. Of course, other means could be provided for cooperating with the wire.

The implant 11 also includes rigid prongs 43 and 45 which are adapted to penetrate the abductor muscle-tendon adjacent the greater trochanter. Although one or more of the prongs 43 and 45 could be provided if desired, preferably at least two of the prongs are provided to assist in fixing the greater trochanter 13 in the desired position. Each of the prongs 43 and 45 has a surface 46 which is sufficiently broad to avoid cutting of the greater trochanter 13. The preferred location for the prongs 43 and 45 is at the end 24 at the opposite ends of the end section 27, and the tunnels extend along the regions of the prongs adjacent the band 15. To facilitate penetration of the abductor muscle-tendon and to enhance rigidity, each of the prongs 43 and 45 preferably tapers toward a point 47 remote from the section 27. Each of the prongs 43 and 45 is preferably curved downwardly slightly as it extends toward the point 47 as best shown in FIG. 3. Generally, however, the prongs 43 and 45 are perpendicular to the plane of the bands 15, 17, 19 and 21.

The implant 11 is used to retain the greater trochanter 13 in position following certain hip surgery in which the greater trochanter has been cut away. FIG. 4 shows the proximal femur 49 near the completion of the surgery with a prosthetic femoral component 51 cemented into the femur and with the greater trochanter 13 being relocated in the femur. The prosthetic femoral component 51 has a femoral head 51 which projects out of the femur 49.

After the greater trochanter 13 is relocated, it can be retained in position with the implant 11 and with elongated elements, such as wires 55, 57 and 59, as shown in FIGS. 5 and 6. This can be accomplished by placing the implant 11 over the greater trochanter 13 and permanently deforming the implant 11 into general conformity with the exterior configuration of the greater trochanter. The wire 55 is passed through a hole 61 which is drilled in the femur 49 and through the eyelets 37, and the ends of the wire 55 are appropriately joined together as by twisting or knotting to form a joint 63. Similarly, the wires 57 and 59 extend through their respective tunnels 39 and 41 and through a hole 65 which is drilled in the femur. The opposite ends of the wires 57 and 59 are suitably joined together to form joints 67 and 69, respectively.

The implant 11 securely retains the trochanter 13 in position and in so doing performs numerous important functions. For example, the wires 55, 57 and 59 overlie the bands 17, 19 and 21, respectively, and extend through the tunnels 39 and 41 so that these bands and tunnels prevent harmful contact between the wires and the greater trochanter. As shown in FIG. 6, the joints 63, 67 and 69 also overlie the bands 17, 19 and 21, respectively. The surfaces 22 and 46 (FIG. 3) of the implant 11 and prongs 43 and 45, respectively, are generally flat and have sufficient surface area so as to avoid cutting or damaging of the trochanter 13.

When in position, the prongs 47 penetrate the abductor muscle-tendon 71 at the proximal end of the trochanter 13. This helps to retain the trochanter 13 in position. Also, because the implant 11 is deformed into general conformity with the trochanter 13, it assumes a dished or hat-like configuration which also tends to hold the implant 11 in position. In extending over the bands 17, 19 and 21 and through the eyelets 37 and the tunnels 39 and 41, the wires 55, 57 and 59 retain the implant 11 in a fixed position on the trochanter 13 and cause the implant to bear tightly against the greater trochanter 13. The implant 11 is preferably large enough to fit over a major portion of the greater trochanter 13 and may be larger in relation to the trochanter than illustrated in FIGS. 5 and 6.

Although an exemplary embodiment of the invention has been shown and described, many changes, modifications and substitutions may be made by those having ordinary skill in the art without necessarily departing from the spirit and scope of this invention.

I claim:

1. An implant for use in retention of the greater trochanter, said implant comprising:

a deformable circumferentially extending band which completely circumscribes a region;

a first deformable band extending between regions of the circumferentially extending band and being joined to the circumferentially extending band at first and second locations, said circumferentially extending band circumscribing at least a length of said first band, said bands being adapted to engage the greater trochanter and to be deformed to approximate the contour of the greater trochanter;

means attached to at least one of said bands for cooperating with at least one elongated element to facilitate tying of the implant in position over the greater trochanter; and means attached to one of said bands for penetrating an abductor muscle-tendon.

2. An implant as defined in claim 1 wherein at least a portion of said cooperating means is adjacent one end of said first band.

3. An implant as defined in claim 1 wherein the circumferentially extending band is elongated and has side sections which are inclined toward each other as they extend in the direction of elongation.

4. An implant for use in retention of the greater trochanter, said implant comprising:

first and second deformable bands, each of said bands having opposite ends, said bands extending in different directions and being joined together at a first location intermediate the ends of said first and second bands;

a deformable circumferentially extending band extending circumferentially completely around the first location and a region of the first and second bands and attached to said first and second bands radially outwardly of said first location, said bands being generally in the same plane and adapted to overlie the greater trochanter and to be deformed to approximate the contour of the greater trochanter;

means attached to at least one of said bands for cooperating with at least one elongated element to facilitate tying of the implant in position over the greater trochanter; and means attached to one of said bands for penetrating an abductor muscle-tendon.

5. An implant as defined in claim 4 wherein said first and second bands extend generally transverse to each other and said implant includes a third band joined to said first band at a second location and extending generally transverse to said first band and said circumferentially extending band circumscribes and joins regions of said first, second, and third bands.

6. An implant as defined in claim 4 wherein said first and second bands extend generally transverse to each other and said implant includes a third band joined to said first band at a second location intermediate the ends of said first and third bands and extending generally transverse to said first band, said penetrating means includes first and second rigid prongs, means for attaching the first and second prongs to the second and third bands with the prongs being generally perpendicular to said plane, respectively, said prongs being adapted to penetrate a muscle-tendon adjacent the greater trochanter and said circumferentially extending band completely circumscribing said second location and major lengths of said first, second and third bands.

7. An implant as defined in claim 6 wherein said second and third bands are generally parallel and are longer than the first band, said first and second locations are farther from said prongs than from the other ends of the second and third bands.

8. An implant as defined in claim 6 wherein said circumferentially extending band is joined to the end portions of the first, second, and third bands and said penetrating means includes means forming tunnels adjacent said prongs.

9. An implant for use in retention of the greater trochanter, said implant comprising:

first and second deformable bands, each of said bands having opposite ends, said bands extending in different directions and being joined together at a first location, said bands being adapted to overlie the greater trochanter and to be deformed to approximate the contour of the greater trochanter;

means attached to said second band for penetrating a muscle-tendon adjacent the greater trochanter; and means attached to said bands for cooperating with an elongated element to facilitate tying of the implant in position over the greater trochanter.

10. An implant as defined in claim 9 wherein said bands extend generally transverse to each other and said implant includes a third band joined to one of said bands at a second location and extending generally transverse to said one band, and means attached to said third band for cooperating with an elongated element for tying the implant in position over the greater trochanter.

11. An implant as defined in claim 10 including means attached to said third band for penetrating a muscle adjacent the greater trochanter.

12. An implant as defined in claim 9 including a deformable circumferentially extending band extending circumferentially and attached to said first and second bands radially outwardly of said first location.

13. An implant as defined in claim 9 wherein said second band is longer than said first band and said first location is spaced from the mid-point of said second band whereby said first location is farther from said penetrating means than from the other end of said second band.

14. An implant as defined in claim 9 wherein said penetrating means includes a prong.

15. An implant as defined in claim 9 wherein said first location is intermediate the ends of said first and second bands.

16. An implant as defined in claim 9 wherein said penetrating means includes a relatively rigid prong having a relatively broad surface for engaging the muscle-tendon and said cooperating means includes means defining a tunnel extending along a region of the prong.

17. An implant comprising:

a circumferential band generally in the form of a rectangle, but having rounded corners, said band having a longitudinal axis and a transverse axis;

a pair of substantially parallel bands extending longitudinally and intersecting at their ends with said circumferential band;

a transverse band offset from the middle of said rectangle toward one end of the rectangle intersecting each of said parallel bands and terminating at each of its ends in said circumferential band;

means adjacent the intersections of said transverse and circumferential bands for receiving an elongated element for affixing the implant in position;

hollow prong means extending generally perpendicular from the other end of the rectangle adjacent the intersections of said parallel and circumferential bands for penetrating a muscle and for receiving an elongated element for further affixing of the implant; and at least said bands being unitarily formed from a deformable material such that they are shapable so as to generally conform to a surface against which the implant is placed.

* * * * *